United States Patent [19]

Snider

[11] Patent Number: 4,488,327
[45] Date of Patent: Dec. 18, 1984

[54] COMBINATION TOOTHBRUSH AND TONGUE SCRAPER

[76] Inventor: C. Jennings Snider, 232 Cherokee Rd., Charlotte, N.C. 28207

[21] Appl. No.: 500,143

[22] Filed: Jun. 1, 1983

[51] Int. Cl.³ ............................................. A46B 9/04
[52] U.S. Cl. ................................... 15/111; 128/304; 248/110; 248/359
[58] Field of Search ............... 15/111, 167 R, 167 A; 128/304, 62 A; 206/478, 479, 480, 481; 248/110-113, 359, 359.1, 360

[56] References Cited

U.S. PATENT DOCUMENTS

| | | | |
|---|---|---|---|
| D. 122,815 | 10/1940 | Crosby | 15/111 |
| 1,470,710 | 10/1923 | Davis | 128/62 A |
| 2,226,409 | 12/1940 | Patterson et al. | 206/478 |
| 2,566,650 | 9/1951 | Anderson | 211/65 |
| 2,651,068 | 9/1953 | Seko | 15/111 |
| 3,254,356 | 6/1966 | Yao et al. | 15/111 |
| 3,890,964 | 6/1975 | Castanedo | 128/304 |

*Primary Examiner*—Peter Feldman
*Attorney, Agent, or Firm*—Bell, Seltzer, Park & Gibson

[57] ABSTRACT

A combination toothbrush and tongue scraper is provided with the tongue scraper comprising a loop having a width greater than that of the handle and possessing sufficient flexural rigidity for the loop to remain open during use and to sufficiently deflect widthwise to allow passage of the tongue scraper through an aperture of a conventional toothbrush holder when in nonuse.

1 Claim, 5 Drawing Figures

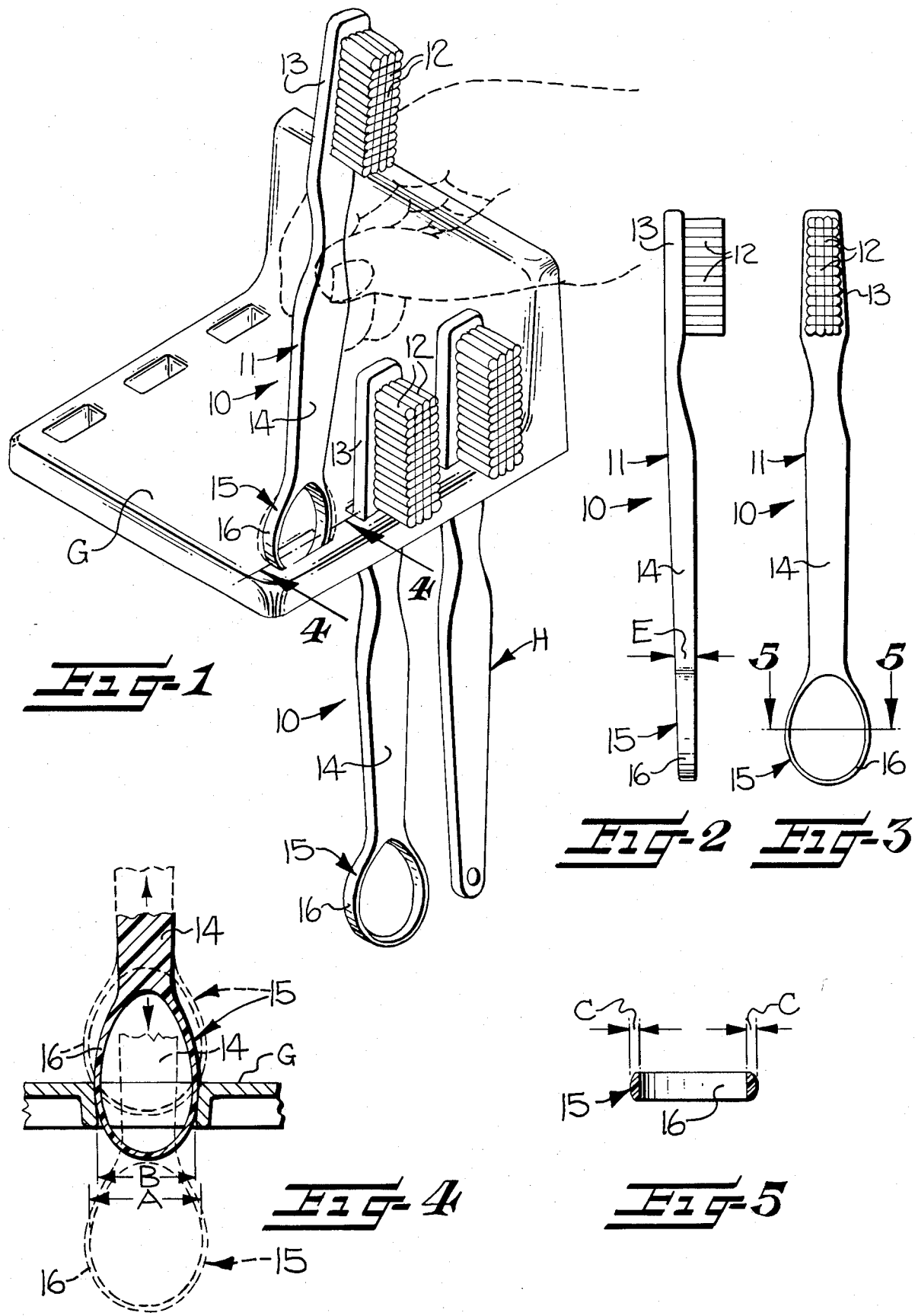

COMBINATION TOOTHBRUSH AND TONGUE SCRAPER

FIELD AND BACKGROUND OF THE INVENTION

The present invention relates to a combination toothbrush and tongue scraper. It has been determined that proper cleaning of the tongue regularly is an important part of oral hygiene. This can best be accomplished by scraping the upper surface of the tongue regularly in conjunction with the brushing of one's teeth. In the past, tongue scrapers have been attached to the end of a toothbrush handle opposite the bristles in such a manner that the device is not well suited to accomplish its purpose as a tongue scraper comfortably, or the scrapers create difficulties in storing the toothbrush in a convenient receptacle, such as a toothbrush holder.

U.S. Pat. No. 1,728,956 issued Sept. 24, 1929, discloses a combination toothbrush and tongue scraper in which the tongue scraper comprises a hoe-type blade fixedly attached transverse of the free end of the toothbrush handle. This device requires the opening of one's mouth to an unnecessary and possibly uncomfortable degree to accommodate to hoe-type scraper blade during use. The sharp corners of the scraping edge of the hoe-type blade also can jab or injure the lower gums or teeth of the user. Moreover, the joint between the hoe-type blade and the toothbrush handle is difficult to clean properly after use.

The combination toothbrush and tongue scraper disclosed in U.S. Pat. No. 2,651,068 issued Sept. 8, 1953 includes a rigid, metallic ring which may be used as a tongue scraper and which is mounted for swivel movement on the toothbrush handle. During the tooth brushing procedure the user inserts a finger into the ring so that the toothbrush handle will rotate to present the bristles in a position normal to tooth surfaces. Such a construction, including crevices surrounding the swivel connection, makes proper cleaning of the device after use more difficult.

The prior art devices described above are further limited in practical application in that both are cumbersome and uncomfortable to the hand of the user during the tooth brushing procedure. Moreover, neither can be stored in a conventional manner such as in a toothbrush holder because of the size and rigidity of the tongue scrapers.

SUMMARY OF THE INVENTION

With the foregoing in mind, it is a primary object of this invention to provide an improved combination toothbrush and tongue scraper in which the width of the tongue scraper increases its effectiveness while remaining comfortable in the hand during the tooth brushing procedure.

A further object of the invention is to provide a combination toothbrush and tongue scraper in which the flexural rigidity of the tongue scraper is such to allow passage of the scraper and toothbrush handle through an aperture of a conventional toothbrush holder.

A more specific object of the invention is to provide a combination toothbrush and tongue scraper, integrally formed, with no cracks, crevices or corners, thereby enabling more efficient cleaning and permitting the invention to be integrally molded, thereby reducing manufacturing costs.

In accordance with this invention, an improved combination toothbrush and tongue scraper is provided which is comfortable in the hand of the user and wherein the tongue scraper comprises a loop having a width greater than the width of the toothbrush handle. The loop is of such a width that it may be used as an efficient tongue scraper, while possessing a flexural rigidity which permits its widthwise deflection when the toothbrush is being passed through the aperture of a conventional toothbrush holder so that the tongue scraper does not prevent storage in the holder during nonuse.

BRIEF DESCRIPTION OF THE DRAWINGS

Some of the objects and advantages of the invention having been stated, others will appear as the description proceeds, when taken in connection with the accompanying drawings, in which FIG. 1 is a perspective view of a conventional toothbrush holder in which a standard toothbrush and the invention are illustrated being stored during nonuse;

FIG. 2 is a side elevational view of the improved combination toothbrush and tongue scraper;

FIG. 3 is a front elevational view thereof;

FIG. 4 is an enlarged sectional view taken along the line 4—4 of FIG. 1 of the tongue scraper portion, particularly illustrating its flexural rigidity as it passes through an aperture of a conventional toothbrush holder; and FIG. 5 is a sectional view taken along the line 5—5 of FIG. 3 of the tongue scraper portion illustrating the cross-sectional shape thereof.

DETAILED DESCRIPTION

Referring more specifically to the drawings, the improved combination toothbrush and tongue scraper, broadly identified by numeral 10, is illustrated in FIG. 1 in storage during nonuse in a conventional toothbrush holder G. From this figure, it may be seen by the two illustrated units of the invention, one in stored condition and one being moved into stored condition, that the invention may be stored in a holder G in the same manner as a standard toothbrush H and that the overall length of the combination toothbrush and tongue scraper 10 and the standard toothbrush H are illustrated as preferably being substantially the same.

Referring particularly to FIGS. 2 and 3, it will be observed that a toothbrush, broadly indicated at 11, is provided with rows of bristles 12 attached to a body 13 in turn connected to an elongate handle 14 at one end thereof. A tongue scraper, broadly indicated at 15, is connected to the other end of the handle 14. The tongue scraper 15 comprises a loop 16 having a greater width than that of the handle 14. The loop 16 is of such an area so as to effectively perform the scraping procedure in less time than if the loop were smaller. Furthermore, the area and cross-sectional shape of the loop 16 are such that less pressure will be applied to the tongue during the procedure, and the tongue scraper 15 will not dig into the tongue or otherwise cause discomfort during use. As depicted in the preferred embodiment, the loop 16 is at least about three-fourths inch in width.

It can further be seen in both FIGS. 2 and 3 that the preferred embodiment of the combination toothbrush and tongue scraper 10, is unitary in construction. As illustrated, the body 13, handle 14 and loop 16 are integrally formed of a plastic material such as generally used in a standard toothbrush body 13 and handle 14, wherein the juncture between said body and handle, and the juncture between said handle and loop are each characterized by being smoothly curved surfaces devoid of any crevices or interruptions.

As illustrated in FIG. 4, the loop 16 of the tongue scraper 15 possesses a flexural rigidity such that its normal width A may be reduced to the width of an aperture B of a conventional toothbrush holder G while passing therethrough. The oval shape of the loop 16 also facilitates such passage through the aperture. Additionally, the oval shape allows the loop 16 to be introduced and guided into the aperture at an angle rather than requiring solely a straight approach. On the other hand, the flexural rigidity of the loop 16 is such that it remains in an open condition during use as a tongue scraper and in a stored condition in a toothbrush holder G. Moreover, the flexural rigidity is such that the loop 16 of the tongue scraper 15 is comfortable in the hand of the user during the tooth brushing procedure. The construction of the loop 16 is such that the wall thickness C of the loop 16, measured in the direction of the width of the loop 16, is less than the thickness E of the handle 14.

As illustrated in FIG. 5, the edges defined by the opposing faces of the loop 16 have a "D" cross-sectional shape, such that the opposing faces of the loop 16 are provided with tapered edges to facilitate scraping. The symmetrical cross-sectional shape of the walls of the loop 16 also allows either side of the loop 16 to be used to perform the scraping function.

Thus it can be seen that this invention overcomes all of the noted deficiencies of earlier mentioned prior art and efficiently and effectively enhances oral hygiene through the scraping of the upper surface of the tongue. At the same time, the flexural rigidity of the loop 16 of the tongue scraper 15 is such that it is comfortable in the hand of the user during the tooth brushing procedure and permits storage of the invention in a conventional holder G.

In the drawings and specification, there has been set forth a preferred embodiment of the invention, and although specific terms are employed, they are used in a generic and descriptive sense only and not for purposes of limitation.

What is claimed is:

1. A toothbrush having a plastic body provided with rows of bristles thereon, an elongate substantially rectangular plastic handle having one end connected to said body, and means defining a plastic tongue scraper connected to and extending from the other end of said handle, said body, handle and tongue scraper being integrally molded of plastic, said means defining said tongue scraper comprising a plastic loop positioned substantially in the widthwise plane of said handle so that the opening through the loop extends in the direction of the thickness of said handle, the juncture between said body and handle, and the juncture between said handle and loop are each characterized by being smoothly curved surfaces devoid of any crevices or interruptions, and wherein the width of the plastic loop is at least about three-fourths inch and is greater than the width of said handle, the wall thickness of said loop measured in the direction of the width of said loop being less than the thickness of said handle measured along the shortest dimension of said handle, said loop being substantially oval shaped in plan to facilitate passage of the loop through aperture of a toothbrush holder, the length of said handle being many times the length of said oval shaped loop taken longitudinally of said handle, the opposing faces of said loop having scraping edges defined by tapered edges, and wherein the flexural rigidity of said plastic loop is such as to maintain the loop in open condition during usage as a tongue scraper and to permit widthwise deflection of the loop to reduce the width of the loop when the toothbrush is being passed through an aperture of a conventional toothbrush holder, whereby the presence of the tongue scraper on the toothbrush does not prevent the toothbrush being stored in a toothbrush holder when in nonuse.

* * * * *